United States Patent
Harrison et al.

(10) Patent No.: US 10,621,414 B2
(45) Date of Patent: Apr. 14, 2020

(54) METHODS AND SYSTEMS FOR IMAGE COLLECTION AND DIMENSIONAL ANALYSIS FOR MEDICAL DIAGNOSES

(71) Applicants: Howard Jason Harrison, Bethesda, MD (US); Ryszard M. Pluta, Bethesda, MD (US)

(72) Inventors: Howard Jason Harrison, Bethesda, MD (US); Ryszard M. Pluta, Bethesda, MD (US)

(*) Notice: Subject to any disclaimer, the term of this patent is extended or adjusted under 35 U.S.C. 154(b) by 0 days.

(21) Appl. No.: 16/278,071

(22) Filed: Feb. 16, 2019

(65) Prior Publication Data
US 2019/0258848 A1 Aug. 22, 2019

Related U.S. Application Data

(60) Provisional application No. 62/632,326, filed on Feb. 19, 2018.

(51) Int. Cl.
*G06T 7/00* (2017.01)
*G06K 9/00* (2006.01)
*G16H 30/20* (2018.01)

(52) U.S. Cl.
CPC ..... *G06K 9/00248* (2013.01); *G06K 9/00261* (2013.01); *G06T 7/0012* (2013.01); *G06K 9/00234* (2013.01); *G16H 30/20* (2018.01)

(58) Field of Classification Search
None
See application file for complete search history.

(56) References Cited

U.S. PATENT DOCUMENTS

2015/0332020 A1* 11/2015 Lo ................. A61K 31/567
702/19

OTHER PUBLICATIONS

Levevre, Ce et al: Telling facial metrics: Facial width is associated with Testosterone levels in man. 2013, Evolution and Human Behavior, 34, 273-269.
https://www.forbes.com/sites/jvchamary/2017/09/16/how-face-id-works-apple-iphone-x/#5bb50e76624d.

* cited by examiner

*Primary Examiner* — Idowu O Osifade
(74) *Attorney, Agent, or Firm* — Spano Law Group; Joseph S. Spano

(57) ABSTRACT

Methods and systems for implementing health monitoring based on changes in body dimensions derived from images of a human collected over long periods of time are presented herein. An image based medical diagnosis system precisely measures body dimensions, changes in body dimensions over time, or both, and identifies whether any measured dimensions, changes in dimensions, or both, have exceeded one or more threshold values indicative of the onset or recurrence of a medically significant condition. In another further aspect, an alert is communicated to medical professionals to further investigate the medical condition of the human user. In one aspect, body dimensions are estimated based on a known value of a reference dimension identifiable in each of the plurality of images. In some examples, the distance between facial features in an image is normalized with respect to the measured inter-pupillary distance associated with that image.

18 Claims, 4 Drawing Sheets

MEMORY
131

| PATIENT CODE | PATIENT IMAGE | TIME | IPD [MM] | EE [MM] | NC [MM] | |
|---|---|---|---|---|---|---|
| A | A12345.BMP | 09/12/2011, 06:14:26 | 64.38 | 141.1 | 69.5 | ~151 |
| A | A25647.BMP | 10/11/2011, 06:10:29 | 64.39 | 141.3 | 69.6 | ~152 |
| A | A28941.BMP | 11/11/2011, 06:19:35 | 64.38 | 141.5 | 69.6 | ~153 |
| ... | ... | ... | ... | ... | ... | |
| A | A65143.BMP | 09/13/2017, 05:45:48 | 64.38 | 145.6 | 69.8 | ~154 |
| A | A69541.BMP | 10/11/2017, 06:24:16 | 64.37 | 145.9 | 69.9 | ~155 |
| A | A72157.BMP | 11/13/2017, 06:56:57 | 64.38 | 146.1 | 69.8 | ~156 |
| ... | ... | ... | ... | ... | ... | |

Columns labeled 104 (PATIENT CODE, PATIENT IMAGE, TIME) and 149 (IPD, EE, NC).

FIG. 3

METHODS AND SYSTEMS FOR IMAGE COLLECTION AND DIMENSIONAL ANALYSIS FOR MEDICAL DIAGNOSES

CROSS REFERENCE TO RELATED APPLICATION

The present application for patent claims priority under 35 U.S.C. § 119 from U.S. provisional patent application Ser. No. 62/632,326, entitled "Image Based Medical Diagnoses," filed Feb. 19, 2018, the subject matter of which is incorporated herein by reference in its entirety.

TECHNICAL FIELD

The described embodiments relate to diagnoses of disease based on images collected over time.

BACKGROUND INFORMATION

Many diseases and health conditions cause changes in facial dimensions. For example, humans afflicted by brain and cranial nerve tumors, Cushing's disease, acromegaly, certain type of stroke or brain infection, etc., exhibit significant changes in facial dimensions over the course of time. Drug abuse by chemicals such as steroids, opiates, etc., also cause significant changes in facial dimensions over the course of time. In one example, over 250,000 people are newly diagnosed with brain tumor related medical conditions every year. Some brain tumor conditions have a time to diagnosis of up to seven years. Thus, brain tumor conditions often remain undiagnosed for several years. The long intervening period between onset and diagnosis often limits treatment options, decreases effectivity, and dramatically increases overall treatment cost. In addition, patients treated for the removal of tumors are monitored for disease recurrence by expensive, time consuming, and stressful blood and imaging (e.g., magnetic resonance imaging) tests.

If facial dimensions are considered at all in a day-to-day medical practice, typically, facial dimensions are examined visually by a physician at the time of a patient visit. Visible facial distortions may be employed by a doctor as one of many clues in a medical diagnosis. However, it is not common for physicians to perform measurements of facial dimensions and track changes in measurements of facial dimensions over time as part of a medical diagnosis. As the retrospective data is typically unavailable, physicians do not use precise measurement and tracking of facial dimensions as part of a medical diagnosis. Small changes in facial dimensions pass unnoticed by a physician in a typical clinical setting. As a result, an often leading indicator of disease is often ignored until a significant period of time passes after onset of the disease.

Improvements in patient health monitoring systems are desired. In particular, improvements in image collection and analysis for medical diagnoses are desired.

SUMMARY

Methods and systems for implementing health monitoring based on body dimensions, changes in body dimensions, or both, derived from images of a human collected over long periods of time are presented herein.

In one aspect, an image based medical diagnosis system is communicatively coupled to one or more image collection devices available to a human user. One or more image collection devices capture images of the human body. The collected images are stored and analyzed.

In a further aspect, images of the body of the human user are collected periodically over a significant period of time (e.g., at least once per month over a period of years). In some embodiments, the image based medical diagnosis system precisely measures facial dimensions and changes in facial dimensions over time and identifies whether any measured dimensions, changes in facial dimensions, or both, have exceeded one or more threshold values indicative of the onset or recurrence of a medically significant condition (e.g., onset or recurrence of disease, tumor, etc.). The one or more dimensions are estimated based at least in part on a known value of a reference dimension identifiable in each of the plurality of images.

In some embodiments, an image based medical diagnosis tool (IBMDT) determines the number of pixels between the pupils (i.e., inter-pupillary distance) located in each image. Based on the known distance between the pupils and the determined number of pixels, the IBMDT estimates a scaling factor that relates actual distance per pixel in each image. In addition, the IBMDT estimates the actual distance between selected facial features based on the number of pixels between the selected facial features located in each image and the scaling factor associated with each image.

In this manner, the distance between any selected facial features in an image is normalized with respect to the measured inter-pupillary distance (IPD) associated with that image. Since the actual IPD is known, the distance between any selected facial features is also determined.

In another further aspect, the image based medical diagnosis system communicates an alert (e.g., to the human user, qualified medical personnel, etc.) indicating abnormal body dimensions, changes in body dimensions, or both. In this manner, the image based medical diagnosis system prompts medical professionals of the need to further investigate the medical condition of the human user.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

BRIEF DESCRIPTION OF THE DRAWINGS

FIG. 3 is a diagram illustrative of a memory 131 storing facial records 151-156, including facial images collected over several years.

DETAILED DESCRIPTION

Reference will now be made in detail to background examples and some embodiments of the invention, examples of which are illustrated in the accompanying drawings.

Methods and systems for implementing health monitoring based on body dimensions, changes in body dimensions, or both, derived from images of a human collected over long periods of time are presented herein.

In one aspect, an image based medical diagnosis system is communicatively coupled to one or more image collection devices available to a human user. In some examples, one or more image collection devices capture images of the face. The collected images are communicated to the image based medical diagnosis system for storage and analysis.

Figure 1:
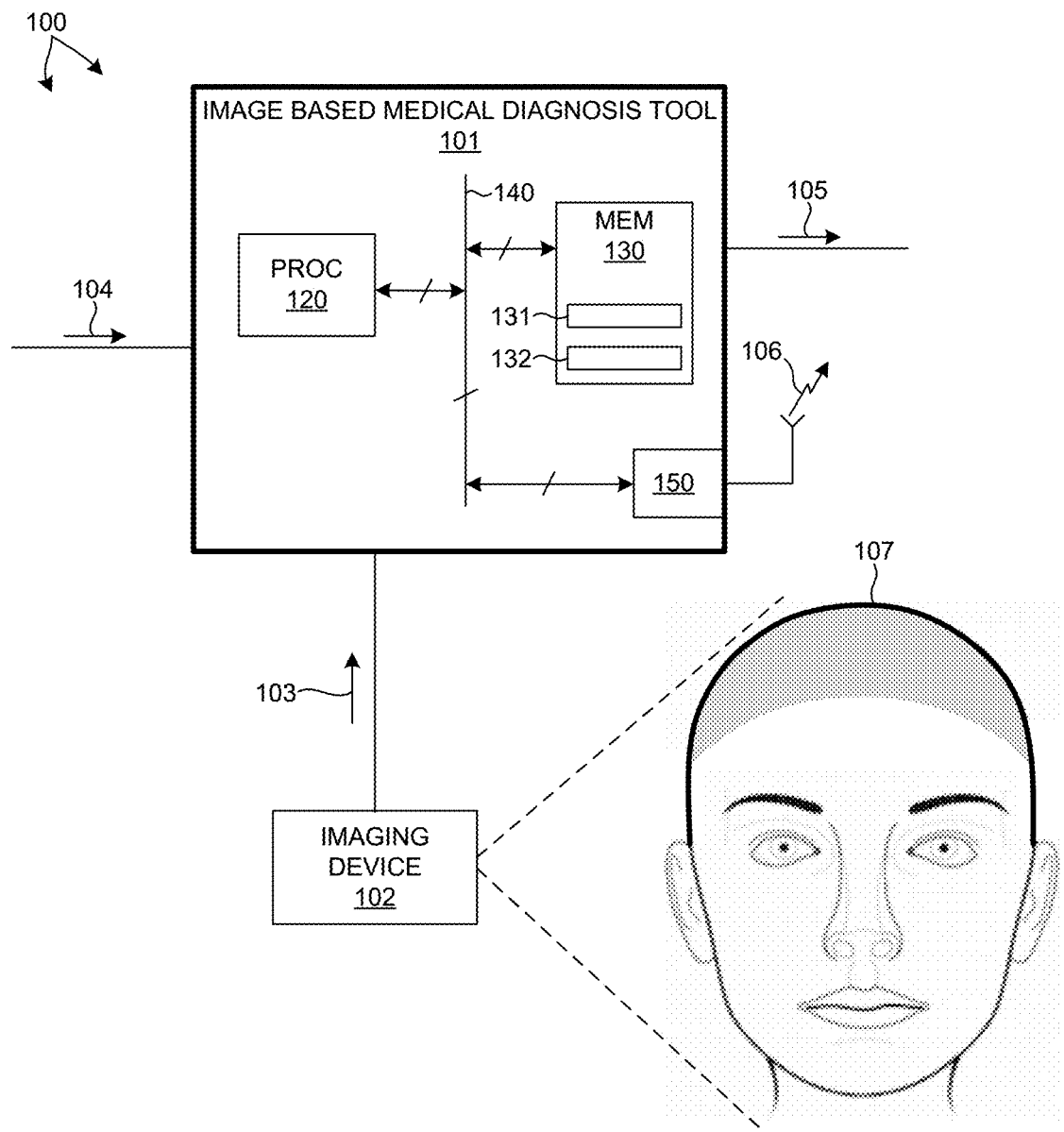
FIG. 1 is a diagram illustrative of an embodiment of an image based medical diagnosis system (IBMDS) 100 including one or more imaging devices 102 and an image based diagnosis tool (IBMDT) 101 in at least one aspect.

FIG. 1 is a diagram illustrative of an embodiment of an image based medical diagnosis system (IBMDS) 100 including one or more imaging devices 102 and an image based diagnosis tool (IBMDT) 101. In the embodiment depicted in FIG. 1, imaging device 102 collects images of the face of a human user 107. The images 103 are communicated to IBMDT 101.

As depicted in FIG. 1, IBMDT 101 includes a processor 120, a memory 130, a bus 140, and a wireless communication transceiver 150. Processor 120, memory 130, and wireless communication transceiver 150 are configured to communicate over bus 140.

As depicted in FIG. 1, IBMDT 101 is configured to receive images 103 from imaging device 102. Memory 130 also includes an amount of memory 132 that stores program code that, when executed by processor 120, causes processor 120 to implement image based medical diagnosis functionality as described herein. Memory 130 also includes an amount of memory 131 that stores measurement data extracted from images 103 by IBMDT 101.

In some embodiments, images of the face of the human user are collected periodically over a significant period of time (e.g., at least once per month over a period of years). The image based medical diagnosis system precisely measures facial dimensions and changes in facial dimensions over time and identifies whether any measured facial dimensions, changes in facial dimensions, or both, have exceeded one or more threshold values indicative of the onset or recurrence of a medically significant condition (e.g., onset or recurrence of disease, tumor, etc.). The one or more dimensions are estimated based at least in part on a known value of a reference dimension identifiable in each of the plurality of images.

Figure 2:
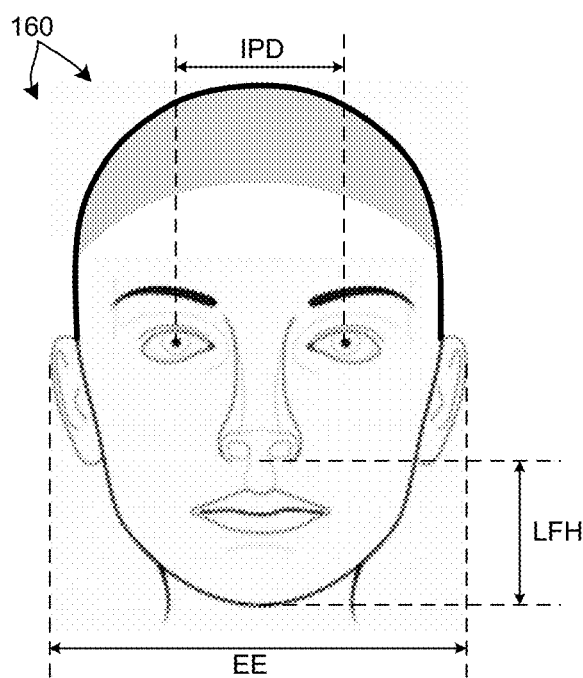
FIG. 2 is a diagram illustrative of an exemplary facial image 160 and dimensions of interest measured by an IBMDS.

In the embodiment depicted in FIG. 1, IBMDT 101 is communicatively coupled to imaging device 102 by a wired communication link. IBMDT 101 receives images 103 and extracts facial dimensions from the collected images. FIG. 2 depicts an exemplary image 160. In one example, IBMDT 101 extracts distances associated with the inter-pupillary distance (IPD), lower facial height (LFH), and ear to ear (EE) distance.

In general, the relationship between image pixel count and actual distance between physical points captured in an (e.g., image 103) varies because each image may be captured at different angles and distances with respect to the face of the user. However, the inter-pupillary distance remains approximately constant over the lifetime of an adult human.

In one aspect, IBMDT 101 determines the number of pixels between the pupils (i.e., inter-pupillary distance) located in each image 103. Based on the known distance between the pupils and the determined number of pixels, IBMDT 101 estimates a scaling factor that relates actual distance per pixel in each image 103. In addition, IBMDT 101 estimates the actual distance between selected facial features based on the number of pixels between the selected facial features located in each image 103 and the scaling factor associated with each image 103.

In this manner, the distance between any selected facial features in an image is normalized with respect to the measured inter-pupillary distance (IPD) associated with that image. Since the actual IPD is known, the distance between any selected facial features is also determined.

Although, the IPD is described hereinbefore as a preferred reference dimension in facial images, in general, any stable facial dimension, or set of markings, captured in an image of the human face may be contemplated as a reference dimension in this patent document. Although, facial dimensions such as ear to ear distance and LFH are described with reference to FIG. 2, in general any suitable dimension may be estimated by IBMDT 101, and any suitable stable body dimension may be employed as a reference dimension.

Furthermore, although the operation of an image based medical diagnosis system is described with reference to facial images, facial dimensions, and facial reference dimensions, in general, the image based medical diagnosis systems described herein may operate based on images of any portion of the human body to track any suitable body dimension provided a reference dimension having a known value is identifiable within each image under consideration.

In general, IBMDT 101 is communicatively coupled to one or more imaging devices 102 by any suitable communication link (e.g., wired or wireless communication link). In some examples, IBMDT 101 and an imaging device 102 are communicatively coupled by a wireless communication link operating in compliance with any suitable wireless communications protocol (e.g., Bluetooth®, WiFi, ZigBee®, any cellular network based protocol, or other communications network). In some other examples, IBMDT 101 and an imaging device 102 are communicatively coupled with a wired communication link operating in compliance with any suitable wired communications protocol (e.g., serial data link, Ethernet®, etc.).

In one example, IBMDT 101 is implemented as part of a portable computing device such as a smart phone, tablet computer system, etc. In many of these examples, the portable computing device integrates an imaging device 102 with a computing system implementing the functionality of IBMDT 101. In other examples, a portable computing device and collected images are uploaded to an external computing system (e.g., external server, cloud based computing system, etc.) via signals 106 communicated from IBMDT 101. In some of these examples, signals 106 are communicated over a wireless communications link (e.g., via wireless transceiver 150 depicted in FIG. 1) or via a wired communications link (e.g., through a wired connection between the portable computing device and a communication network (e.g., the Internet, etc.).

In general, imaging device 102 includes any suitable imaging device a user 107 may employ to collect facial images. In some examples, imaging device 102 collects two dimensional images of the face of user 107. In these examples, imaging device 102 includes a two dimensional image sensor (e.g., charge coupled device, complementary metal oxide on silicon device, etc.)

In some of these examples, IBMDT 101 generates a three dimensional model of the human face based on a sequence of images collected by imaging device 102 from different angles with respect to the human face. Distances between selected facial features are determined by IBMDT 101 based on the three dimensional model. As described hereinbefore, the distance between any selected points in the three dimensional model is normalized with respect to a reference distance (e.g., the measured IPD) associated with that three dimensional model. Since the actual IPD is known, the distance between any selected facial features is also determined.

In some of these examples, imaging device 102 is a three dimensional imaging device, such as a scanning laser based imaging device. In one embodiment imaging device 102 is a "structure sensor" manufactured by Occipital, Inc., San Francisco, Calif. (USA). In other embodiments, imaging device 102 is a LIDAR based sensor. In these embodiments, the three dimensional imaging device 102 generates a three dimensional point cloud of image data 103 that is communicated to IBMDT 101. In other embodiments, imaging device 102 is a three dimensional camera system, such as the TrueDepth® camera system manufactured by Apple, Inc., Cupertino, Calif. (USA) that is integrated with portable computing devices manufactured by Apple Inc., such as the iPhoneX®.

In one embodiment a portable computing device, such as a smartphone, tablet computer, etc., implements IBMDT functionality as described with respect to FIG. 1 based on three dimensional images 103 collected from a three dimensional imaging device.

In another aspect, IBMD system 100 collects facial images and estimates facial dimensions at multiple points in time over a substantially long period. In some examples, facial images are collected and facial dimensions are estimated one or more times per day, week, or month, over a period of years. FIG. 3 depicts an illustration of memory 131. As depicted in FIG. 3, memory 131 stores facial records 151-156 including facial images collected over several years, the time of image acquisition, and the estimated facial dimensions.

In another further aspect, the image based medical diagnosis system communicates an alert (e.g., to the human user, qualified medical personnel, etc.) indicating abnormal facial dimensions, changes in facial dimensions, or both. In this manner, the image based medical diagnosis system prompts medical professionals of the need to further investigate the medical condition of the human user.

As depicted in FIG. 1, processor 120 is configured to process the digital images generated by imaging device 102 and generate an alert if the one or more of the estimated facial dimensions or change in facial dimension exceeds one or more predetermined threshold values. In one example, an alert is communicated if a measured facial dimension differs from an average facial dimension (e.g., average LFH, average EE, etc.) by a predetermined threshold value. In another example, processor 120 is configured to process the digital images generated by imaging device 102 to detect anomalies that may indicate an imminent, or on-going medical health emergency. In the event such an anomaly is detected, processor 120 communicates an alarm message 105 (e.g., audibly via a speaker of the portable computing device, visually via a display of the portable computing device, over the Internet, etc.) to an entity able to address the medical issue. In one example, processor 120 receives a digital image 103 and estimates an abnormal change in EE distance indicative of a brain tumor. In this example, processor 120 generates an alarm message 105 that is communicated to a medical doctor associated with the medical care of the human user 107. For example, IBMDT 101 may send an e-mail, text, or phone message to a physician, a close relative, etc. indicating the nature of the medical emergency.

In some examples, IBMDS 100 identifies changes in dimensions of features of a human user (e.g., facial dimensions) that are indicative of tumor onset or recurrence after treatment. In some examples, hormonally active pituitary gland tumors (e.g., adenoma secreting growth hormone) evoke characteristic changes in the shape of the human face (e.g., Cushing's moon face or acromegaly). Typically, these tumors are very small (e.g., 3-5 mm in diameter), and reside in a pituitary gland. For these reasons, these tumors are often difficult to detect and resect completely. In many cases, patients treated by surgery see an initial reversal of facial changes. However, in some cases symptoms slowly recur. This may occur over a period of several years. In these examples, IBMDS 100 may identify early symptoms of tumor recurrence based on changes of facial dimensions measured in accordance with the methods and systems described herein. In this manner, patient anxiety evoked by frequent follow-up visits and tests and time and cost associated with these visits are avoided.

In some other examples, IBMDS 100 identifies changes in dimensions of features of a human user (e.g., facial dimensions) that are indicative of heart failure. Examples of features measured by IBMDS 100 indicative of enhanced risk of heart failure include the dimension of diagonal creases on the earlobes, i.e., Frank's sign, xanthomas appearing on eyelids, a grey ring around the outside of the iris, a.k.a., arcus senilis.

In another further aspect, IBMDT 101 receives a query 104 from a concerned entity (e.g., human user 107, a medical professional associated with the medical care of human user 107, etc.). In response to the query 104, IBMDT 101 communicates an indication 105 of the health status of the human body to the requesting entity including estimated facial dimensions, their changes over time, or both.

In some examples, IBMDS 100 is implemented as part of a portable computing device such as a smart phone, tablet computer system, etc. In some of these examples, IBMDS 100 is configured to capture images of the human user 107 automatically when the desired portion of the body of human user 107 (e.g., the face of human user 107) is within the field of view of the imaging device 102 of the portable computing system. For example, when a human user 107 visually engages with the portable computing device for any purpose (e.g., interact with a software application, dial a phone number, compose or read a text message, etc.), the IBMDS 100 is configured to collect images of the face of human user 107, identify whether the reference feature(s) (e.g., IPD) and any desired features (e.g., LFH, EE, etc.) are present in the collected images, and store images that include one or more reference features and one or more desired features. In some other examples, IBMDS 100 prompts the human user 107 to: 1) locate the portable computing device such the desired portion of the body of the human user 107 is within the field of view of an imaging device of the portable computing system, and 2) instruct the portable computing device to collect one or more images of the human user 107. In some examples, IBMDS 100 may prompt a human user to collect one or more images on a periodic basis (e.g., every hour, every day, etc.). In other examples, IBMDS 100 may prompt a human user to collect one or more images in response to a request from a query 104 from a medical professional.

In some examples, IBMDS 100 is implemented as part of portable computing device integrating three dimensional (3D) display capabilities such as virtual reality goggles, etc. In these examples, an imaging device integrated with the three dimensional display captures images of the face of the human user 107 and estimates facial images such as IPD, pupil size, etc. In one of these examples, the images captured by the 3D display system are analyzed by IBMDT 101 to determine whether a human user wearing the 3D display is undergoing an epileptic seizure based on measured pupil size.

Figure 4:
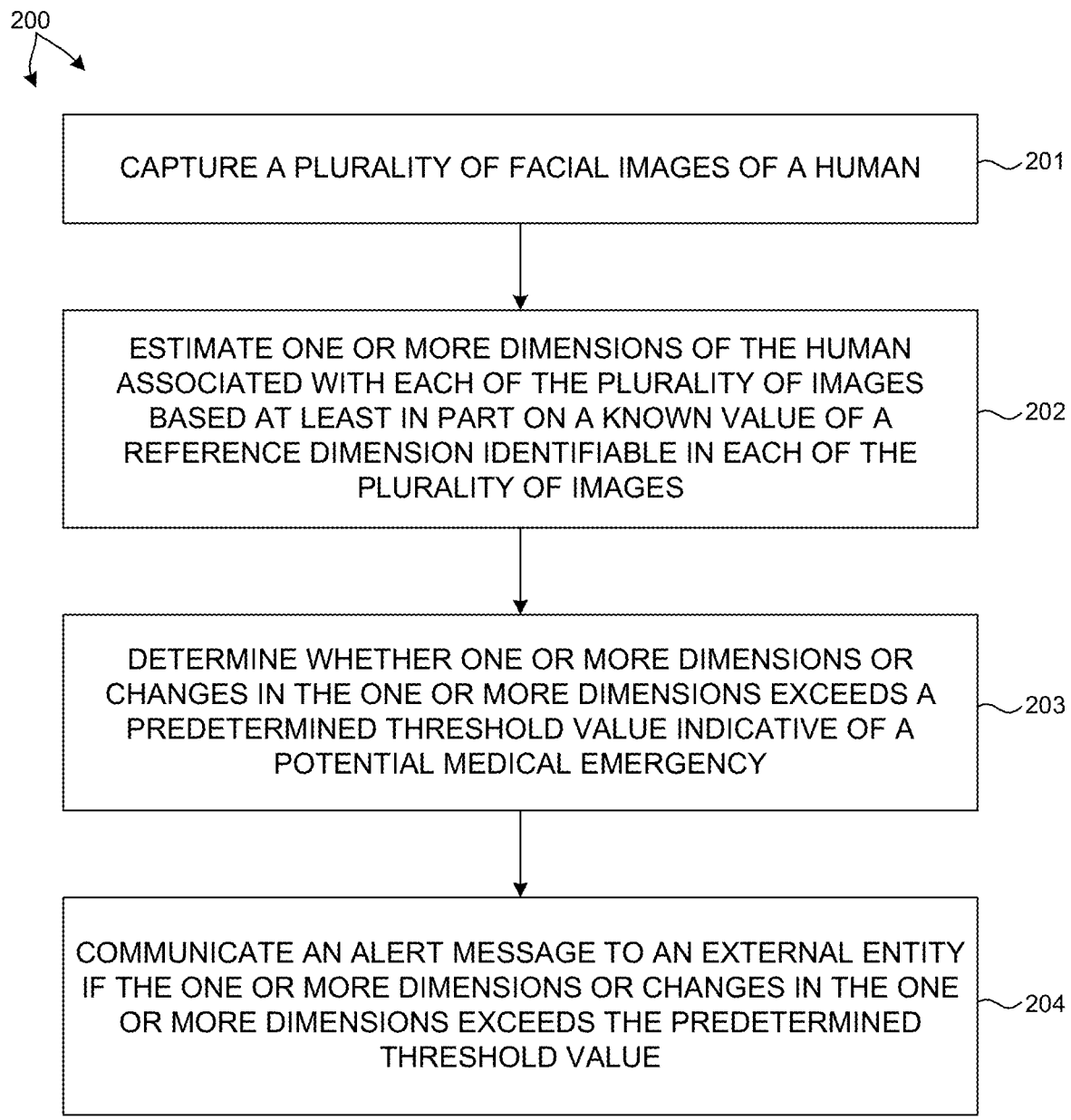
FIG. 4 is a flowchart illustrative of a method 200 implementing health monitoring and communications gateway functionality as described herein.

FIG. 4 illustrates a flowchart of a method 200 implementing health monitoring and communications gateway functionality as described herein. In some embodiments, IBMDS 100 is operable in accordance with method 200 illustrated in FIG. 4. However, in general, the execution of method 200 is not limited to the embodiments of IBMDS 100 described with reference to FIG. 1. This illustration and corresponding explanation are provided by way of example as many other embodiments and operational examples may be contemplated.

In block 201, a plurality of facial images of a human is captured by an imaging device.

In block 202, one or more dimensions of the human associated with each of the plurality of images are estimated. The one or more dimensions are estimated based at least in part on a known value of a reference dimension identifiable in each of the plurality of images.

In block 203, it is determined whether one or more dimensions, or changes in the one or more dimensions, exceeds a predetermined threshold value indicative of a potential medical emergency.

In block 204, an alert message is communicated to an external entity if the one or more dimensions, or changes in the one or more dimensions, exceeds the predetermined threshold value.

In one or more exemplary embodiments, the functions described may be implemented in hardware, software, firmware, or any combination thereof. If implemented in software, the functions may be stored on or transmitted over as one or more in or code on a computer-readable medium. Compute-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A portable image based medical diagnosis system, comprising:
    an imaging device configured to capture a plurality of images of a human user;
    a processor configured to estimate one or more dimensions of the human user associated with each of the plurality of images based at least in part on a known value of a reference dimension identifiable in each of the plurality of images and determine whether one or more dimensions or changes in the one or more dimensions exceeds a predetermined threshold value indicative of a potential medical emergency, wherein the estimating of the one or more dimensions associated with each of the plurality of images involves determining a number of pixels between a set of reference features located in each image and estimating a scaling factor based on a known distance between the set of reference features and the determined number of pixels; and
    a communication interface configured to communicate an alert message to an external entity if the one or more dimensions or changes in the one or more dimensions exceeds the predetermined threshold value.

2. The portable image based medical diagnosis system of claim 1, further comprising:
    a memory configured to store a time of acquisition of each of the plurality of images and the one or more dimensions associated with each of the plurality of images.

3. The portable image based medical diagnosis system of claim 2, wherein the imaging device, the processor, and the memory are integrated as part of a portable computing system.

4. The portable image based medical diagnosis system of claim 2, wherein the processor, and the memory are integrated as part of a network based computing system separate from the imaging device.

5. The portable image based medical diagnosis system of claim 1, wherein the imaging device is a two dimensional imaging device.

6. The portable image based medical diagnosis system of claim 1, wherein the imaging device is a three dimensional imaging device.

7. The portable image based medical diagnosis system of claim 1, wherein the plurality of images are collected at multiple points in time over a substantially long period.

8. The portable image based medical diagnosis system of claim 7, wherein the substantially long period of time exceeds one year.

9. The portable image based medical diagnosis system of claim 1, wherein the set of reference features includes the eye pupils of a human user.

10. A method comprising:
    capturing a plurality of images of a human;
    estimating one or more dimensions of the human associated with each of the plurality of images based at least in part on a known value of a reference dimension identifiable in each of the plurality of images, wherein the estimating of the one or more dimensions associated with each of the plurality of images involves determining a number of pixels between a set of reference features located in each image and estimating a scaling factor based on a known distance between the set of reference features and the determined number of pixels;

determining whether one or more dimensions or changes in the one or more dimensions exceeds a predetermined threshold value indicative of a potential medical emergency; and communicating an alert message to an external entity if the one or more dimensions or changes in the one or more dimensions exceeds the predetermined threshold value.

11. The method of claim 10, further comprising:

storing a time of acquisition of each of the plurality of images and the one or more dimensions associated with each of the plurality of images.

12. The method of claim 10, wherein each of the plurality of images is a two dimensional image.

13. The method of claim 10, wherein each of the plurality of images is a three dimensional image.

14. The method of claim 10, wherein the plurality of images are collected at multiple points in time over a substantially long period.

15. The method of claim 14, wherein the substantially long period of time exceeds one year.

16. The method of claim 10, wherein the set of reference features includes the eye pupils of a human user.

17. A portable image based medical diagnosis system, comprising:

an imaging device configured to capture a plurality of images of a human user;

a non-transient, computer readable medium storing instructions that when read by a processor cause the processor to:

estimate one or more dimensions of the human user associated with each of the plurality of images based at least in part on a known value of a reference dimension identifiable in each of the plurality of images, wherein the estimating of the one or more dimensions associated with each of the plurality of images involves determining a number of pixels between a set of reference features located in each image and estimating a scaling factor based on a known distance between the set of reference features and the determined number of pixels; and determine whether one or more dimensions or changes in the one or more dimensions exceeds a predetermined threshold value indicative of a potential medical emergency; and a communication interface configured to communicate an alert message to an external entity if the one or more dimensions or changes in the one or more dimensions exceeds the predetermined threshold value.

18. The portable image based medical diagnosis system of claim 17, wherein the imaging device, the processor, and the memory are integrated as part of a portable computing system.

* * * * *